(12) United States Patent
Blomquist

(10) Patent No.: US 9,135,393 B1
(45) Date of Patent: *Sep. 15, 2015

(54) PROCESSING PROGRAM DATA FOR MEDICAL PUMPS

(75) Inventor: Michael L. Blomquist, Andover, MN (US)

(73) Assignee: Smiths Medical ASD, Inc., Rockland, MA (US)

( * ) Notice: Subject to any disclaimer, the term of this patent is extended or adjusted under 35 U.S.C. 154(b) by 562 days.

This patent is subject to a terminal disclaimer.

(21) Appl. No.: 09/631,000

(22) Filed: Aug. 2, 2000

(51) Int. Cl.
*G06F 19/00* (2011.01)

(52) U.S. Cl.
CPC .................................. *G06F 19/00* (2013.01)

(58) Field of Classification Search
USPC ........ 705/2–4; 600/300; 180/98; 364/413.02; 128/630; 604/31; 395/610; 709/203
See application file for complete search history.

(56) References Cited

U.S. PATENT DOCUMENTS

| | | | |
|---|---|---|---|
| 3,734,229 A * | 5/1973 | Comer .......................... | 180/168 |
| 4,810,243 A | 3/1989 | Howson | |
| 4,847,764 A | 7/1989 | Halvorson | |
| 5,153,827 A * | 10/1992 | Coutre et al. ................. | 604/111 |
| 5,155,847 A | 10/1992 | Kirouac et al. | |
| 5,307,262 A * | 4/1994 | Ertel ................................ | 705/2 |
| 5,338,157 A | 8/1994 | Blomquist | |
| 5,368,562 A * | 11/1994 | Blomquist et al. .............. | 604/65 |
| 5,376,070 A * | 12/1994 | Purvis et al. .................... | 604/31 |
| 5,429,602 A | 7/1995 | Hauser | |
| 5,485,408 A | 1/1996 | Blomquist | |
| 5,643,212 A | 7/1997 | Coutré et al. | |
| 5,658,250 A * | 8/1997 | Blomquist et al. .............. | 604/65 |
| 5,681,285 A | 10/1997 | Ford et al. | |
| 5,685,844 A | 11/1997 | Marttila | |
| 5,687,717 A * | 11/1997 | Halpern et al. ................ | 600/300 |
| 5,713,856 A * | 2/1998 | Eggers et al. ................... | 604/65 |
| 5,729,735 A * | 3/1998 | Meyering ............................. | 1/1 |
| 5,737,539 A | 4/1998 | Edelson et al. | |

(Continued)

FOREIGN PATENT DOCUMENTS

| | | |
|---|---|---|
| CA | 2485024 | 11/2003 |
| JP | 7502678 | 3/1995 |

(Continued)

OTHER PUBLICATIONS

Anonymous, "Acute healthcare Solutions' Dosewatch to use Multum's MediSource", PR Newswire, Feb. 26, 2998, 3 pages.*

(Continued)

*Primary Examiner* — John Pauls
(74) *Attorney, Agent, or Firm* — Patterson Thuente Pedersen, P.A.

(57) ABSTRACT

An apparatus for maintaining a library of program data for medical pumps, the apparatus comprising: memory loaded with a database, the database including a plurality of program data records and a plurality of data key records, each program data record containing a set of program data items, at least some of the program data items included in the database for controlling operation of a medical pump, each data key record containing a data key and each data key identifying one of the data program records; a database management system programmed to link a data key to a set of program data; and a scanner in data communication with the database management system, the database management system being further programmed to receive a code scanned by the scanner, save the code in a data key record, and link the code to a set of program data, the code being a data key.

10 Claims, 10 Drawing Sheets

(56) References Cited

U.S. PATENT DOCUMENTS

| | | | |
|---|---|---|---|
| 5,781,442 A | | 7/1998 | Engelson et al. |
| 5,788,669 A | * | 8/1998 | Peterson .................. 604/65 |
| 5,807,336 A | | 9/1998 | Russo et al. |
| 5,833,599 A | | 11/1998 | Schrier et al. |
| 5,857,967 A | | 1/1999 | Frid et al. |
| 5,875,242 A | | 2/1999 | Glaser et al. |
| 5,885,245 A | * | 3/1999 | Lynch et al. .................. 604/67 |
| 5,935,099 A | | 8/1999 | Peterson et al. |
| 5,940,623 A | | 8/1999 | Watts et al. |
| 5,950,190 A | | 9/1999 | Yeager et al. |
| 6,012,034 A | | 1/2000 | Hamparian et al. |
| 6,222,482 B1 | | 4/2001 | Gueziec |
| 6,269,340 B1 | * | 7/2001 | Ford et al. .................. 705/3 |
| 6,363,282 B1 | * | 3/2002 | Nichols et al. .................. 607/30 |
| 6,421,650 B1 | | 7/2002 | Goetz et al. |
| 6,714,969 B1 | | 3/2004 | Klein et al. |
| 6,790,198 B1 | | 9/2004 | White et al. |
| 6,852,104 B2 | | 2/2005 | Blomquist |
| 7,018,361 B2 | | 3/2006 | Gillespie et al. |
| 7,103,578 B2 | | 9/2006 | Beck et al. |
| 7,384,410 B2 | | 6/2008 | Eggers et al. |
| 7,835,927 B2 | | 11/2010 | Schlotterbeck et al. |
| 8,250,483 B2 | | 8/2012 | Blomquist |
| 2002/0002326 A1 | | 1/2002 | Causey et al. |
| 2002/0029776 A1 | | 3/2002 | Blomquist |
| 2002/0065879 A1 | * | 5/2002 | Ambrose et al. .................. 709/203 |
| 2003/0076792 A1 | | 4/2003 | Theimer |
| 2003/0144880 A1 | | 7/2003 | Talachian et al. |
| 2003/0145053 A1 | | 7/2003 | Bodin et al. |
| 2003/0163088 A1 | | 8/2003 | Blomquist |
| 2003/0163223 A1 | | 8/2003 | Blomquist |
| 2003/0204413 A1 | | 10/2003 | Riff |
| 2003/0204415 A1 | | 10/2003 | Knowlton |
| 2003/0204416 A1 | | 10/2003 | Radpay et al. |
| 2004/0010425 A1 | | 1/2004 | Wilkes et al. |
| 2004/0019607 A1 | | 1/2004 | Moubayed et al. |
| 2004/0172302 A1 | | 9/2004 | Martucci et al. |
| 2004/0249673 A1 | | 12/2004 | Smith |
| 2005/0102167 A1 | | 5/2005 | Kapoor |
| 2005/0143864 A1 | | 6/2005 | Blomquist |
| 2005/0177395 A1 | | 8/2005 | Blomquist |
| 2005/0246416 A1 | | 11/2005 | Blomquist |
| 2006/0047538 A1 | | 3/2006 | Condurso et al. |
| 2006/0229557 A1 | | 10/2006 | Fathallah et al. |
| 2008/0033361 A1 | | 2/2008 | Evans et al. |
| 2008/0034323 A1 | | 2/2008 | Blomquist |
| 2008/0126969 A1 | | 5/2008 | Blomquist |
| 2011/0060758 A1 | | 3/2011 | Schlotterbeck et al. |
| 2011/0282691 A1 | | 11/2011 | Coffman et al. |
| 2013/0012878 A1 | | 1/2013 | Blomquist |
| 2013/0012880 A1 | | 1/2013 | Blomquist |
| 2013/0015980 A1 | | 1/2013 | Evans et al. |
| 2013/0018315 A1 | | 1/2013 | Blomquist |
| 2013/0131630 A1 | | 5/2013 | Blomquist |
| 2014/0094744 A1 | | 4/2014 | Blomquist |
| 2014/0094764 A1 | | 4/2014 | Blomquist |
| 2014/0095485 A1 | | 4/2014 | Blomquist |
| 2014/0095499 A1 | | 4/2014 | Blomquist |
| 2014/0195954 A1 | | 7/2014 | Doshi |

FOREIGN PATENT DOCUMENTS

| | | |
|---|---|---|
| JP | 10143573 | 5/1998 |
| JP | 11502132 | 2/1999 |
| JP | 11505352 | 5/1999 |
| JP | 2002291706 | 10/2002 |
| WO | WO9613790 | 5/1996 |
| WO | WO 99/32031 | 7/1999 |
| WO | WO 00/03344 | 1/2000 |
| WO | WO 00/18449 | 4/2000 |
| WO | WO0211049 | 2/2002 |
| WO | WO03094075 | 11/2003 |

OTHER PUBLICATIONS

"Credit Card Terminals Are Growing Up;" by Lauri Giesen; Credit Card Management, vol. 4, No. 2, p. 96-100; May 1991; ISSN 0896-9329. Dialog ID Number: 00561033. From Dialog File 15: ABI/Inform.*

Configuring a Network Bridge, Windows server. (2003).

Jovanov, et al., "Patient Monitoring Using Person Area Networks of Wireless Intelligent Sensors", Biomedical Sciences Instrumentation. vol. 37 pp. 373-378. (2001).

www.activejump.com published on Dec. 12, 2002 as per wayback engine.

Japanese Decision of Refusal for Japanese Application No. 2011-240566 drafting date Dec. 18, 2013.

Canadian Office Action from Canadian Application No. 2,548,256 dated Apr. 8, 2014.

Australian Examiner's Report No. 3 for Australian Application No. 2011218603 dated Feb. 4, 2014.

Notification of Reasons for Refusal for Japanese Application No. 2011177880 dated Jan. 6, 2014. English Translation is provided.

Australian Notice of Acceptance for Australian Application No. 2012216290 dated Apr. 3, 2014.

European Communication for European Application No. 05713999.0-1951 dated May 27, 2014.

Canadian Office Action for Canadian Application No. 2552580 dated Jun. 23, 2014.

Australian Examiner's first report on Patent Application No. 2004296794 dated Dec. 3, 2009.

Notification of Reasons for Refusal for Japanese Application No. 2006-542752 dated Jun. 23, 2010.

Decision of Refusal for Japanese Application No. 2006542752 dated Jun. 27, 2011.

Notification of Reasons for Refusal for Japanese Application No. 2011-240566 dated Feb. 15, 2013.

Canadian OA for Canadian Application No. 2548256 dated Oct. 23, 2012.

European Communication for European Application No. 04812832.6-1225 dated Oct. 30, 2012.

Canadian OA for Canadian Application No. 2552580 dated Jul. 15, 2013.

Notification of Reasons for Refusal for Japanese Patent Application No. 2011177880 date of dispatch Feb. 12, 2013.

Decision of Refusal for Japanese Application No. 2006-542752 dispatch date Jul. 4, 2011.

Examiner's first report No. 4 on Australian patent application No. 2005216321 dated Aug. 25, 2011.

Examiner's report No. 3 on patent application No. 2005216321 by SmithsMedical ASD, Inc. dated Apr. 20, 2011. Australian Government IP.

Decision of Refusal for Japanese Application No. 2006554321 dispatch date Apr. 18, 2011.

Examiner's report No. 2 on patent application No. 2005216321 by SmithsMedical ASD, Inc. dated Jan. 7, 2011. Australian Govermnment IP.

Notification of Reasons for Refusal for Japanese Patent Application No. 2006-554321 dispatch date Apr. 19, 2010.

Examiner's first report on patent application No. 2005216321 by Smiths Medical ASD, Inc. dated Nov. 26, 2009. Australian Government IP.

Merrit, "Wireless Hospital, Health Care Products on the Upswing", TechWeb. http://www.techweb.com/article/printableArticleSrc.jhtml?articleID=26803705, 2 pages. Jan. 7, 2004.

Steinfeld, "Internet-appliance Technology Automates Test Equipment", EDN, www.ednmag.com. pp. 157-169. Oct. 12, 2000.

Steinfeld, "Is Embedded Going Net-Crazy?", A Response,"TechonLine", 1 page. Mar. 29, 2001.

European Communication for European Application No. 090088220-1952 dated Nov. 15, 2013.

Application and File History for U.S. Appl. No. 11/066,425, filed Feb. 22, 2005, inventor Blomquist.

Application and File History for U.S. Appl. No. 11/003,147, filed Dec. 3, 2004, inventor Blomquist.

(56) References Cited

OTHER PUBLICATIONS

Application and File History for U.S. Appl. No. 13/619,740, filed Sep. 14, 2012, inventor Blomquist.

Application and File History for U.S. Appl. No. 13/619,647, filed Sep. 14, 2012, inventor Blomquist.

Application and File History for U.S. Appl. No. 09/920,467, filed Aug. 1, 2001 inventor Blomquist.

Canadian Office Action from Canadian Application No. 2,552,580 dated Sep. 5, 2012.

User Information CADD-DIPLOMAT™ PC Communications System, 6 pages, copyright 1998, dated Mar. 1998.

Screen Prints from CADD-DIPLOMAT™ PC Communications System CD-ROM, 15 pages. (CD-ROM came with Exhibit A), copyright 1998, dated Mar. 1998.

CADD-DIPLOMAT™ PC Communications System Product Brochure, 4 pages, copyright 1998, dated Jun. 1998.

User Information CADD-DIPLOMAT™ PC Communications System, 7 pages, copyright 1999, dated Nov. 1999.

Application and File History for U.S. Appl. No. 14/035,071, filed Sep. 24, 2013 inventor Blomquist.

Application and File History for U.S. Appl. No. 14/035,380, filed Sep. 24, 2013 inventor Blomquist.

Application and File History for U.S. Appl. No. 14/035,510, filed Sep. 24, 2013 inventor Blomquist.

Application and File History for U.S. Appl. No. 14/035,581, filed Sep. 24, 2013 inventor Blomquist.

* cited by examiner

PROCESSING PROGRAM DATA FOR MEDICAL PUMPS

TECHNICAL FIELD

The present application relates to pumps for infusing fluids into a patient, and more particularly to processing data for programming pumps.

BACKGROUND

There are a variety of different techniques and devices for infusing fluids, such as drugs or nutritional supplements, into a patient. One type of device that is used is an ambulatory drug pump. Such pumps are structured to pump an agent into a patient from a reservoir such as a cassette that attaches to the pump or an I.V. bag. Such a pump is versatile. They can be used for bed-ridden patients in a hospital or nursing home or they can be used for patients that are mobile and have a need to move freely.

Additionally, these pumps are programmable so that they can deliver different types of agents and administer different types of therapies. For example, the pumps can be programmed to deliver nutritional supplements for a parenteral nutritional therapy, drugs for a chemotherapy therapy, pain-relief medication for a pain-control therapy for patient controlled analgesia program, and antibiotics for treating infections.

These pumps may need to be programmed with a variety of program data before each use. Such program data might include delivery schedules and routines; data about the patient such as age, weight, or special medical conditions; and data about the agent such as dose and type of drug.

A difficulty with these systems is that only one item of program data can be entered into the pump at a time—and then usually through a keyboard on the pump. Some systems allow the program data to be entered into the pump via a computer. But even these systems require the caregiver to load only one data item at a time into the pump. Programming the pump in this manner can require both a significant amount of time and caregiver training. Furthermore, many therapies and drugs require different pumps to be repeatedly programmed with the same sets of program data. This process is very time consuming and inefficient. Given the rising cost of health care, efficiency and increased automation are very important.

SUMMARY

One aspect of the present invention is a method for creating a library of pump data on a computer having a database. The pump data is organized into sets of program data. Each set of program data is available for batch downloading to a medical pump and includes data items for controlling operation of the medical pump. The method comprises: entering a plurality of data items into a database on the computer, the plurality of data items forming a set of program data, at least some of the data items establishing parameters for controlling operation of a medical pump; and assigning at least one data key to the set of program data, the data key identifying the set of program data.

An alternative aspect of the invention is an apparatus for maintaining a library of program data for medical pumps. The apparatus comprises memory loaded with a database. The database includes a plurality of program data records and a plurality of data key records. Each program data record contains a set of program data items, and at least some of the program data items included in the database are for controlling operation of a medical pump. Each data key record contains a data key and each data key identifies one of the data program records. A database management system is programmed to link a data key to a set of program data.

Yet another alternative aspect of the invention is directed to an apparatus for batch programming a medical pump. The apparatus comprises memory loaded with a database. The database includes a plurality of program data records and a plurality of data key records. Each program data record contains a set of program data items, and at least some of the program data items included in the database are for controlling operation of a medical pump. Each data key record contains a data key and each data key identifies one of the data program records. A data output is configured for data communication with a programmable medical pump, and a processor is in electrical communication with the memory and the data output. The processor is configured to retrieve a set of program data from the database and batch download the set of program data to the medical pump.

Still another aspect of the present invention is a method for batch programming a medical pump. The method comprises selecting a set of program data, the set of program data including data items for controlling operation of a medical pump; and batch downloading the set of program data to the medical pump, wherein the set of program data is downloaded to the medical pump without intervening action by a user after the first data item is downloaded to the computer.

DETAILED DESCRIPTION

Figure 1:
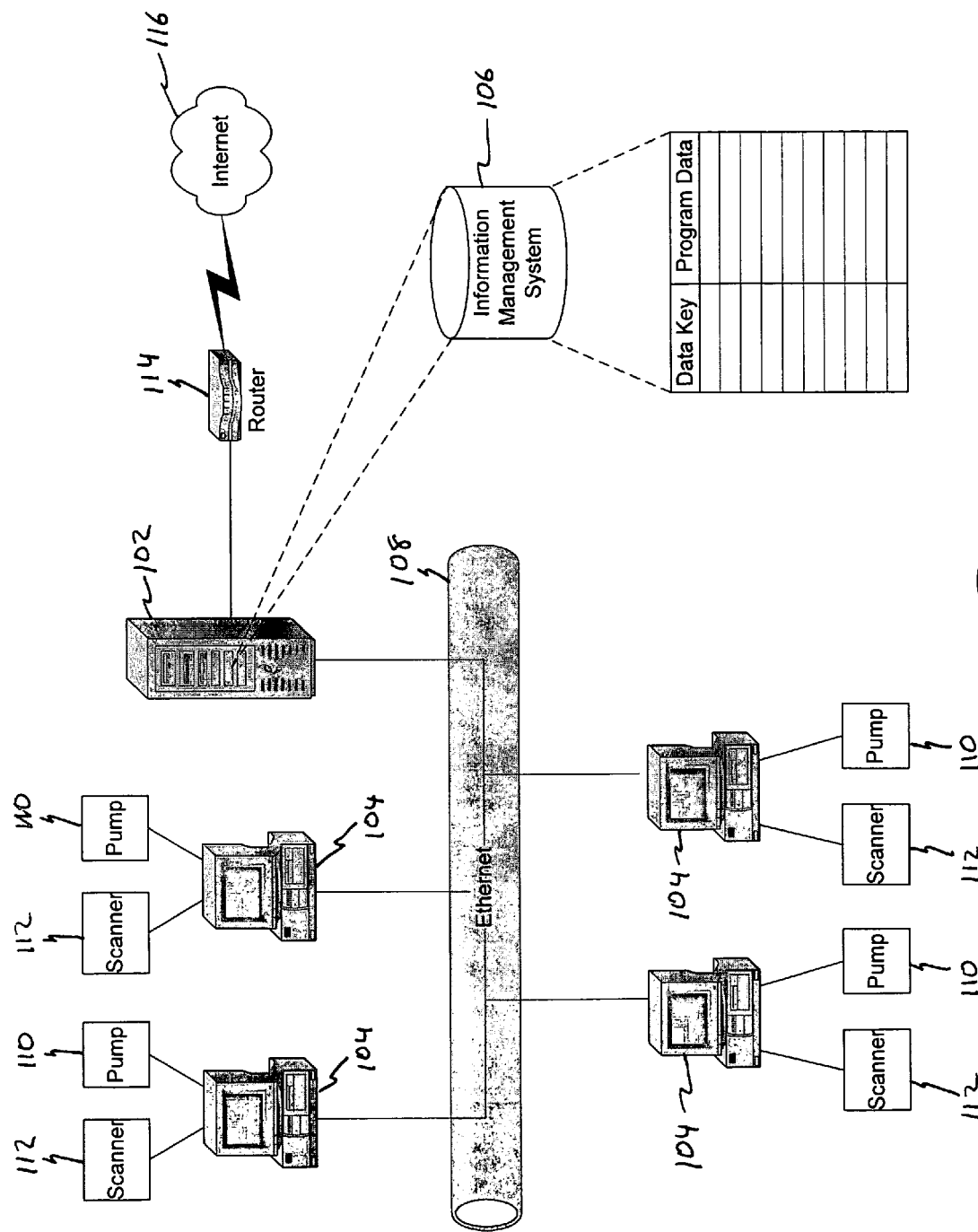
FIG. 1 illustrates one possible environment in which the present invention can be embodied.

A preferred embodiment of the invention will be described in detail with reference to the drawings, wherein like reference numerals represent like parts and assemblies throughout the several views. Reference to the preferred embodiment does not limit the scope of the invention, which is limited only by the scope of the claims attached hereto.

In general terms, the present invention is directed to processing program data for a medical pump. The program data is stored in a database and includes a set of program data and a data key for referencing each set of program data. The set of program data includes data for programming the pump. Examples of the type of data that it can include includes parameters about the patient such as age and weight, delivery schedules, dose requirements, parameters limiting the size and frequency of a bolus the patient can self administer, and the like.

In one aspect of the invention, a caregiver generates a database that includes sets of program data and data keys that identify each set of program data. In another aspect of the invention, the caregiver can then select a data key and load the program data associated with that key into the pump, thereby programming the pump without having to individually reenter each data item into the pump. Examples of data keys that can be used to identify sets of program data include patient names, drug names, or therapy names. Although particular aspects of the invention are discussed above, one skilled in the art will realize that many other aspects of the present invention are disclosed throughout this disclosure.

The following discussion is intended to provide a brief, general description of a suitable computing environment in which the invention may be implemented. Although not required, the invention will be described in the general context of computer-executable instructions being executed by a hand-held computer. The structure, creation, and use of a message store hierarchical folder structure are described after the discussion of an exemplary operating environment.

Additionally, the logical operations of the various embodiments of the invention described herein are implemented as: (1) a sequence of computer implemented steps running on a computing system; and/or (2) interconnected machine modules within the computing system. Modules represent functions executed by program code such as the code found in a dynamic-link library (DLL). The implementation used is a matter of choice dependent on the performance requirements of the pump and the computing systems with which it interfaces. Accordingly, the logical operations making up the embodiments of the invention described herein are referred to alternatively as operations, steps, or modules.

FIG. 1 illustrates one possible computing environment in which the present invention can be embodied. Although one particular type of networking environment and computing platform is illustrated, one skilled in the art will realize that the invention can be embodied using any type of networking environment and computing platform. The invention can even be embodied on an individual, non-networked computer. In essence, the invention can be embodied using any type of computing platform and configuration that includes memory for storing a database and an interface for a programmable pump.

A client/server network system generally shown as 100, comprises a network server 102 and a plurality of computers 104 such as desktop personal computers linked to a client/server network 108. The network server 102 and the individual computers 104 include an operating system and memory. As explained in more detail below, memory on the server 102 is loaded with an information management system 106 having data keys and program data.

Additionally, the client/server network 108 can have any type of configuration. For example, the client/server network connections can be a local area network (LAN) using topologies such as Ethernet or token-ring, a wide area network (WAN), the Internet, or an Intranet. Additionally, the client/server network 108 can be linked to the Internet 116 via a router 114 and server 102.

At least one of the computers 104 connected to the client/server network 108 is configured to be connected to a medical pump 110 such as the Prizm® pump, which is commercially available from Sims Deltec, Inc. of St. Paul, Minn. The interface between the pump 110 and the computer 104 is serial and complies with the RS 232 communication standard, although other communication protocols and interface configurations can be used. Furthermore, the communication link can be a physical cable, a radio frequency (RF) link, or an infrared (IR) link.

At least one of the computers 104 is also in communication with a scanner 112. In one possible embodiment, the scanner 112 is hand-held so that it can be easily used to scan barcodes physical objects such as I.V. bags, medicine packages, patient wristbands, and the like. Again, the communication link between the 112 scanner and the computer 104 complies with the RS 232 communication standard. The communication link between the scanner 112 and the computer 104 can be a physical link, an RF link, or an IR link. Other embodiments use a scanner other than a handheld scanner.

Figure 2:
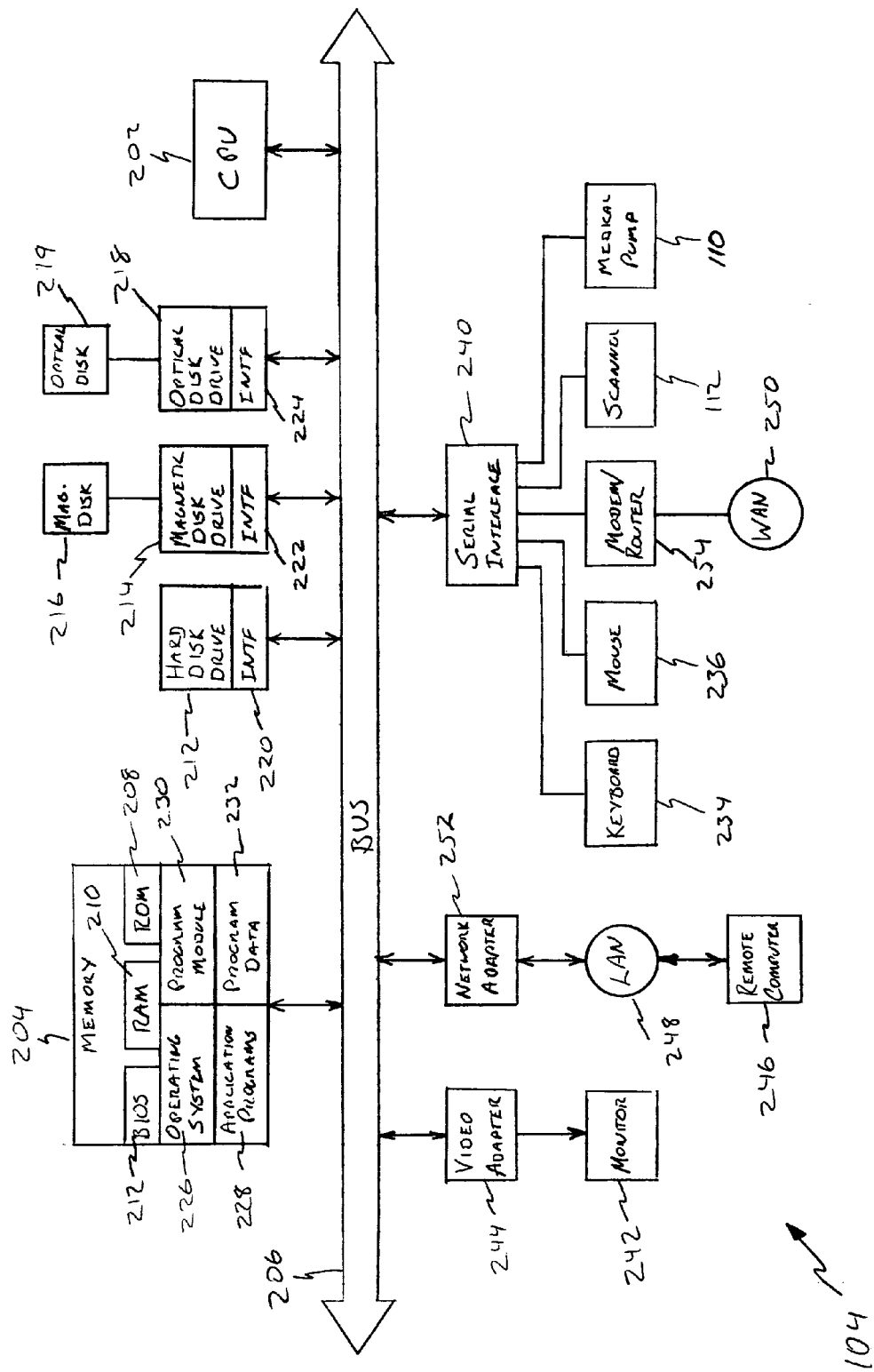
FIG. 2 is a block diagram illustrating architecture for the computer shown in FIG. 1.

FIG. 2 illustrates one possible computer architecture and environment that can be used by computers to embody the present invention. Computer 104 is a conventional personal computer and includes a processor unit 202, a system memory 204, and a system bus 206 that couples various system components including the system memory 204 to the processor unit 202. The system bus 206 may be any of several types of bus structures including a memory bus or memory controller, a peripheral bus and a local bus using any of a variety of bus architectures. The system memory includes read only memory (ROM) 208 and random access memory (RAM) 210. A basic input/output system 212 (BIOS), which contains basic routines that help transfer information between elements within the personal computer 200, is stored in ROM 208.

The memory also includes an operating system, application programs, program modules, and program data. The operating system is a program that controls and allocates usage of the computer's hardware services. The application program includes a kernel for managing memory, manages peripheral devices, launches applications, and allocates resources. Application programs are programs designed to assist the performance of specific tasks other than operation of the computer itself. The program modules includes utilities and other programs that are designed to perform specific tasks such as testing data, system diagnostics, communication protocols, and the like.

The computer 104 further includes a hard disk drive 212 for reading from and writing to a hard disk, a magnetic disk drive 214 for reading from or writing to a removable magnetic disk 216, and an optical disk drive 218 for reading from or writing to a removable optical disk 219 such as a CD ROM, DVD, or other optical media. The hard disk drive 212, magnetic disk drive 214, and optical disk drive 218 are connected to the system bus 206 by a hard disk drive interface 220, a magnetic disk drive interface 222, and an optical drive interface 224, respectively. The drives and their associated computer-readable media provide nonvolatile storage of computer readable instructions, data structures, programs, and other data for the computer 104.

Although the exemplary environment described herein employs a hard disk, the removable magnetic disk 216, removable optical disk 219, and other types of computer-readable media capable of storing data can be used in the exemplary system. Examples of these other types of computer-readable mediums that can be used in the exemplary operating environment include magnetic cassettes, flash memory cards, digital video disks, Bernoulli cartridges, random access memories (RAMs), and read only memories (ROMs).

A number of program modules may be stored on the hard disk 212, magnetic disk 216, optical disk 219, ROM 208 or RAM 210, including an operating system 226, one or more application programs 228, other program modules 230, and program data 232. A user may enter commands and information into the computer 104 through input devices such as a keyboard 234 and mouse 236 or other pointing device. Examples of other input devices may include a microphone, joystick, and scanner. These and other input devices are often connected to the processing unit 202 through a serial port interface 240 that is coupled to the system bus 206. As discussed above, this interface can be a physical connection, RF, or IR. These input devices also may be connected by other interfaces, such as a parallel port or a universal serial bus (USB).

Output devices are also connected to the system bus 206 via an interface or driver. Examples of an output device include a monitor 242 or other type of display device is also connected to the system bus 206 via an interface, such as a video adapter 244. In addition to the monitor 242, personal computers typically include other peripheral output devices (not shown), such as speakers and printers. Another example of an output device is the medical pump 112, as described herein, and a hand-held computer (not shown) that synchronizes with the computer 104. Some devices such as the medical pump 112 and hand-held computer can serve as both input and output devices.

Additionally, the term hand-held computer is used broadly to mean any type of portable computing platform that can interface with the computer. Examples include both hand-held and palm-held computers executing the Windows CE™, Pocket PC™ or Palm™ operating systems. An example of such a palm-held computer is the Symbol PPT 2700 Series Pocket PCs, which includes an integrated scanner and has wireless LAN connectivity. The Symbol PPT 2700 is available from Symbol Technologies, Inc. or Holtsville, N.Y.

As discussed above, the computer 104 may operate in a networked environment using logical connections to one or more remote computers, such as a remote computer 246. The remote computer 246 may be another personal computer, a server, a router, a network PC, a peer device or other common network node, and typically includes many or all of the elements described above relative to the computer 104. The network connections include a local area network (LAN) 248 and a wide area network (WAN) 250. Such networking environments are commonplace in offices, enterprise-wide computer networks, intranets, and the Internet.

When used in a LAN networking environment, the computer 104 is connected to the local network 248 through a network interface or adapter 252. When used in a WAN networking environment, the computer 104 typically includes a modem or other means (e.g., router 114) for establishing communications over the wide area network 250, such as the Internet 116. The modem 254 is connected to the system bus 206 via the serial port interface 240. In a networked environment, program modules depicted relative to the personal computer 200, or portions thereof, may be stored in the remote memory storage device. It will be appreciated that the network connections shown are exemplary, and other means of establishing a communications link between the computers may be used.

One skilled in the art will recognize that the computer architecture illustrated in FIG. 2, on architectures similar thereto, can be used for the server 102 and for mobile computing platforms. Additionally, this architecture is exemplary only and the computers 106, server 102, and hand-held computers can be implemented using different architectures.

FIGS. 3-6 illustrate one possible architecture for the medical pump 110. Although a specific architecture is disclosed herein, one skilled in the art will realize that the present invention can be embodied with any type of programmable pump and that many different pump architectures are possible. In addition to the description set forth herein, additional information about programmable medical pumps and related technologies is set forth in U.S. Pat. No. 5,935,099, issued on Aug. 10, 1999, the disclosure of which is hereby incorporated by reference.

Figure 3:
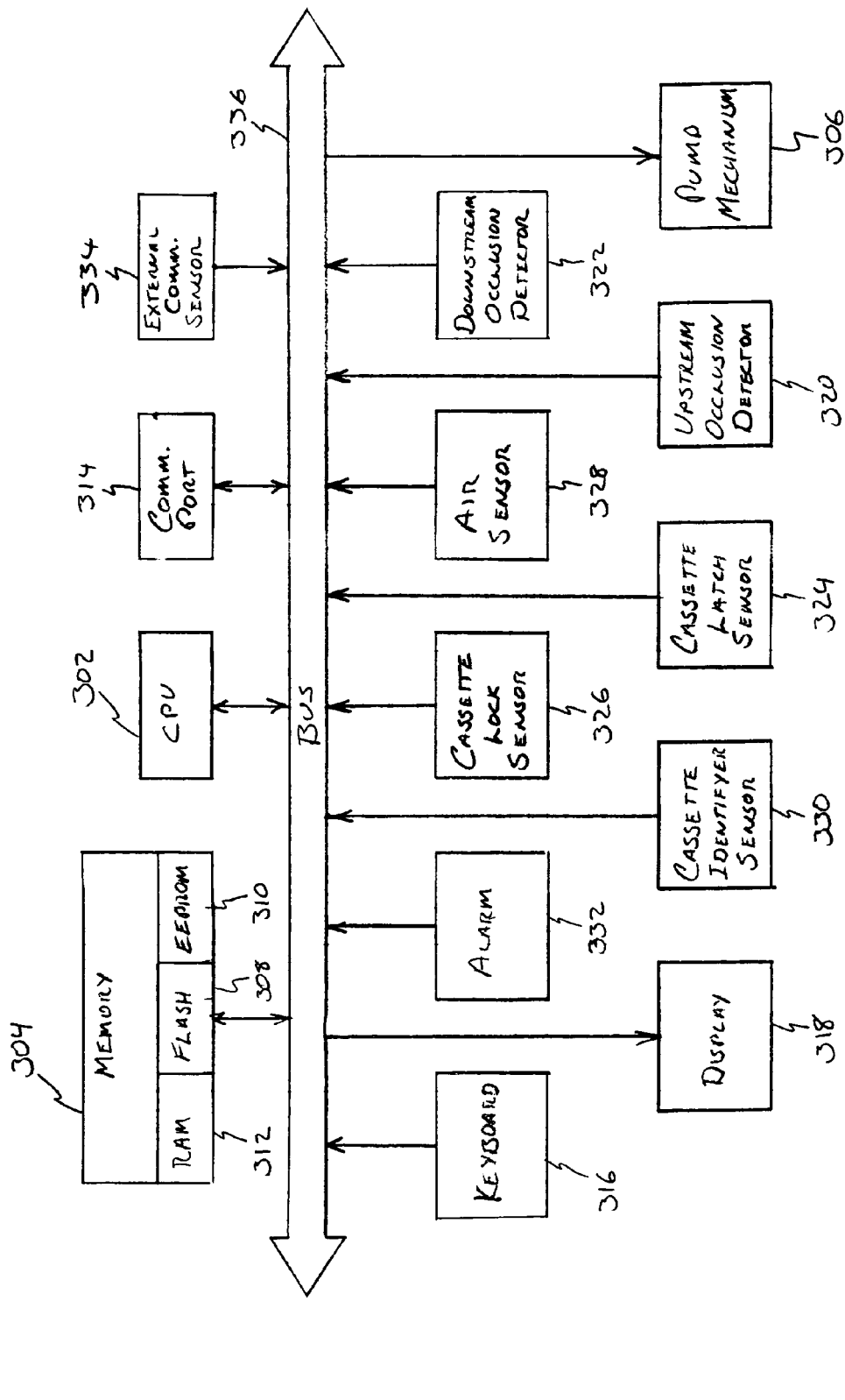
FIG. 3 is a block diagram illustrating architecture for the pump shown in FIG. 1.

FIG. 3 is a schematic of one possible control system 300 for the pump 110. Control system 300 controls operation of pump 110, and includes a microprocessor 302 and a memory system 304 programmable with program data for controlling operation of pump mechanism 306 and the other features of pump 110. A housing can contain the control system 300 and the pump mechanism 306 therein.

Memory system 304 stores various programs and program data related to the operation of pump 110, and is coupled to microprocessor 302, which in turn runs the desired operating programs that control operation of pump mechanism 306. Memory system 304 can include several different types of memory including a flash memory unit 308, electrically erasable programmable read only memory (EEPROM) 310, and a static random access memory (RAM) 312. The program to permit communication with devices external to pump 110 is stored in memory system 304.

Access to microprocessor 302 is provided through communications port 314. As discussed above, communications port 314 is a standard RS232 communications port, although other communication protocols and links are possible (e.g., RF and IR). Information programmed into memory system 304 instructs information to be transmitted or received via communications port 314. This feature allows information being received via communications port 314 from an external device to control pump 110. This feature also allows for the downloading of any or all information from memory system 304 to an external device.

Control system 300 also includes keyboard 316 or other operator input structure for providing information to microprocessor 302. When a key is pressed on keyboard 316, the key sends a signal to microprocessor 302 indicative of the key being pressed. Microprocessor 302 responds to the signal received in the desired manner. Other such input structures may include knobs, buttons, or other like structures for performing pump functions, such as starting, stopping, and priming pump 110.

Display 318 of control system 300 includes structure for displaying information to the patient or caregiver. In one possible embodiment, the display 318 is a liquid crystal display ("LCD") having a 4-line×21-character alpha/numeric display capable of creating 5×7 pixel characters. Display signals sent from microprocessor 302 permit display of information related to the operation of pump 110.

Pump 110 also may be provided with a variety of sensors, switches, or other devices (hereinafter "sensors"). The type of sensors provided depends on the type of pump and its intended use. An example of such sensors includes occlusion detectors 320 and 322 for detecting occlusions in tubing used to infuse fluid from a reservoir to a patient. Further examples of desirable sensors for pump 110 include a cassette latch sensor 324 for indicating whether a latch that latches the cassette to the control module on the pump 110 is open or closed, a cassette lock sensor 326 for indicating whether the latch is locked, an air sensor 328 for detecting air in tubing, and a cassette identification sensor 330. The sensors typically send a suitable electrical signal to microprocessor 302 indicative of the condition sensed. Microprocessor 302 and memory 304 are appropriately programmed to receive and process such signals.

Pump 110 also may be equipped with alarm 332, such as a visual alarm (e.g., L.E.D.'s) and/or an audible alarm (e.g., beeper), which is activated by the sensing of one of the conditions mentioned above, or other conditions. Alarm 332 may be activated as a result of other triggering events, such as error conditions with respect to the power supply or pump hardware. Alarm signals sent from microprocessor 302 permit activation of alarm 332.

In addition, external communication sensor 334 senses when a communications cable connection or powered external serial device connection is made with respect to pump 110 at communications port 314. An appropriate signal is generated by external communication sensor 334 and sent to processor 302 indicative of the connection and/or the lack of connection with the communications cable or other connection device. In one possible embodiment, when a connection is detected, the microprocessor 302 will generate a flag that is communicated to the computer 104 and indicative of a data communication. The flag serves as a handshake that hails the computer. The pump also enters into a connect mode, which is explained in more detail later.

Optionally, external communication sensor 334 can sense when a remote dose cord is attached, or when a remote data-gathering device (e.g., temperature sensor, blood pressure monitor, EKG monitor, or respiratory monitor) is attached. The remote dose cord also can be used by the patient as an event marker for storage in pump memory 304. For example, the patient can use the remote dose cord to note a nauseous condition.

The various sensors, switches, and devices that form or interface with the pump 110 generate and/or receive an appropriate signal or signals during communication with microprocessor 302 during operation of pump 110. Microprocessor 302 is electrically interconnected through an appropriate interface bus 336 with all of the various sensors, switches, and other devices of pump 112. Microprocessor 302 responds to input signals by generating appropriate control output signals in accordance with the program control logic stored in memory. One microprocessor 302 that may be used in connection with pump 110 is an MC68HC11E9 high-density complimentary metal-oxide semiconductor (HCMOS) high performance microcontroller unit (MCU) by Motorola. Such processor includes 512 bytes of electrically erasable programmable read only memory (EEPROM), and 512 bytes of random access memory (RAM). Other types of central processing units or programmable circuitry, such as a microcomputer can be used in place of the microprocessor 302.

Figure 4:
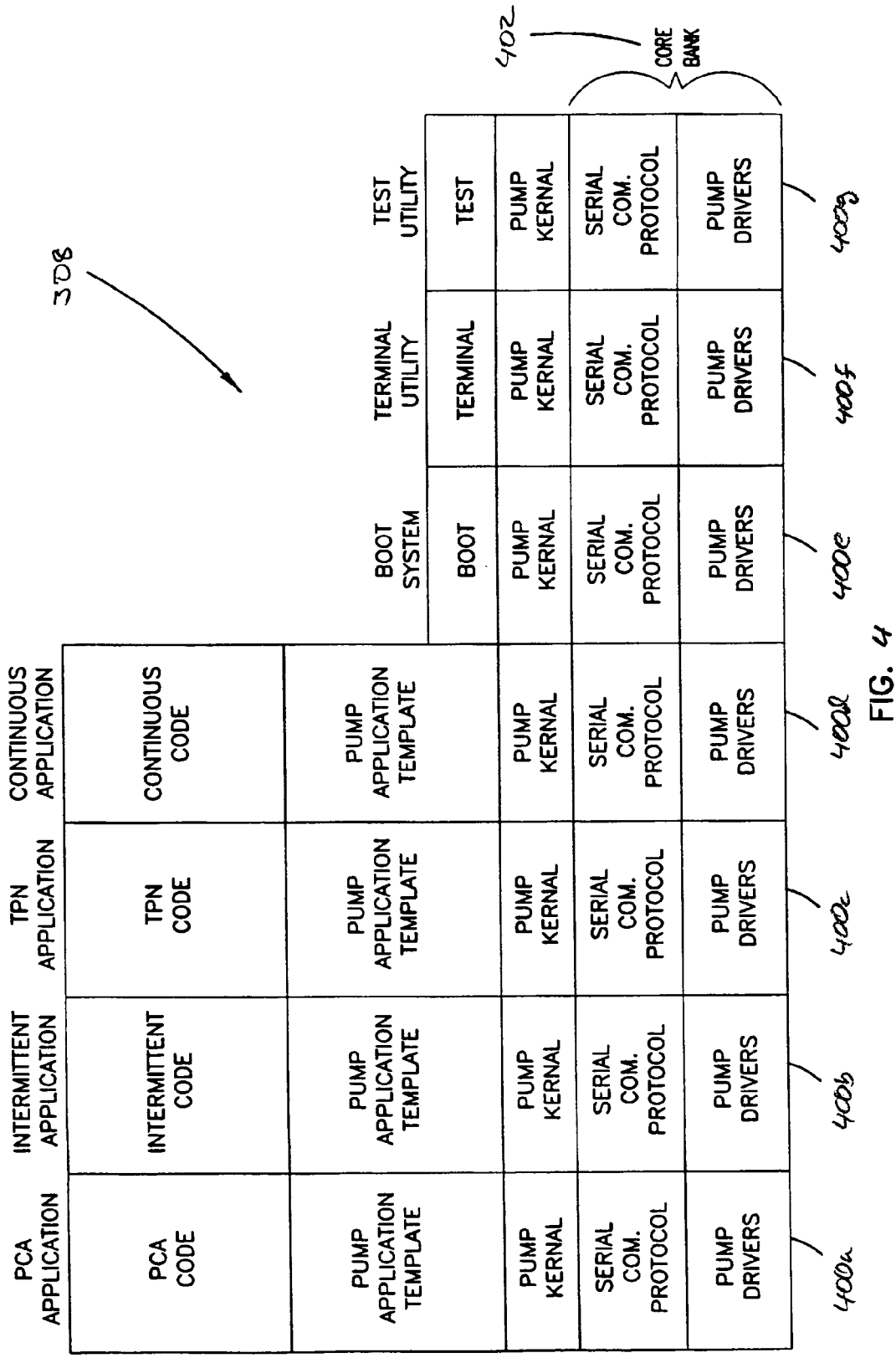
FIGS. 4-6 illustrate a memory map for the pump shown in FIG. 3.

FIG. 4 illustrates how the flash memory 308 is partitioned. Specifically, the flash memory 240 includes seven program slots 400a-400g for storing a boot system program, four application programs, a terminal utility program, and a testing utility program. The application programs include a PCA application, which is for delivering drugs such as pain relief medication; an intermittent application, which is for intermittent delivery of drugs such as antibiotics; TPN application program, which is for administering fluids such as nutrients; and a continuous application program, which is for continuous administration of drugs such as chemotherapy medication.

Physically, the flash memory 308 is divided into sixteen banks. Each application program occupies three banks, each utility slot occupies one bank and the boot system occupies one bank. Additionally, the flash memory 308 includes a core bank 402. Although the programs stored in the flash memory are separate entities, they all share the core bank 402. The core bank 402 is used to store pump drivers, a serial communication protocol, and a portion of the pump kernel. The code stored in the core bank is shared by all of the programs.

Each application program, such as the PCA application, includes an application template, application-specific code, a pump kernel, a serial communication protocol, and pump drivers. The application program controls the pump 110 after being launched by the boot system and performs additional self-tests. The pump application program then begins a review sequence during which various screens are generated and displayed showing the current values of selected application parameters.

Additionally, each application program is the final arbiter of what data can and cannot be downloaded from the information management system 106. In one possible embodiment, accordingly, each application program contains code for testing the data to determine whether it is valid data and is not corrupt.

Upon launching an application program, the pump 110 will automatically stop the pump 110 so that it is not in the normal pumping mode and the pump mechanism 306 does not pump fluid. The caregiver can then program delivery parameters that control how the pump 110 delivers fluid after it is restarted by pressing the START/STOP key. While the pump 110 is running, it is in the normal pumping mode. The pump 110 will deliver fluid and keep track of delivery with status parameters while in the normal pumping mode. In one possible embodiment, none of the application parameters are changeable while the pump 110 is in the normal pumping mode.

The pump application template is a portion of the application program that provides consistency among the various pump application programs. It defines all standard application items, and the user interface structure that each application must follow to create custom application items. Standard application items define the characteristics of each application and can be supplanted with or added to by the application-specific program. The basic tasks performed by the pump application template include:

1. providing all standard menus and help screens, which are available for any specific pump application to use;
2. providing all standard application features, which are available for any specific pump application to use;
3. providing all standard application delivery, status, and configuration parameters, which are available for any specific pump application to use; and
4. providing all standard application alarms, which are available for any specific pump application to use.

The application-specific code is a portion of application program that provides custom application items that are particular to the specific application. The application-specific code is used to customize the pump's 110 behavior and can be programmed only while the pump 110 is stopped. Custom application items may either replace or supplement the standard items provided by the pump application template. Basic tasks performed by a specific pump application include:

1. providing all custom menus and help screens to the kernel, including a start up menu to the kernel that lists the name and/or number of the specific pump applications;
2. providing all custom application features;
3. providing all custom application delivery, status, and configuration parameters to the kernel; and
4. providing all custom application alarms.

Additionally, each application program is an event driven system. The pump drivers provide all hardware interfaces, and the pump kernel provides support services that include an event scheduling and a dispatching system. The serial communication protocol provides serial communication services with peripherals that are connected to the communications port 314.

A terminal utility is formed from the terminal code, the drivers, the kernel, and the serial communication protocol. The terminal controls the external modem and one of the applications running in the pump 110 via the remote serial connection while program data is being downloaded to the memory system 304.

A testing utility is formed from the testing code, the drivers, the kernel, and the serial communication protocol. The testing utility is a stand-alone program that performs various tests on the pump hardware during closed-loop testing.

Figure 5:
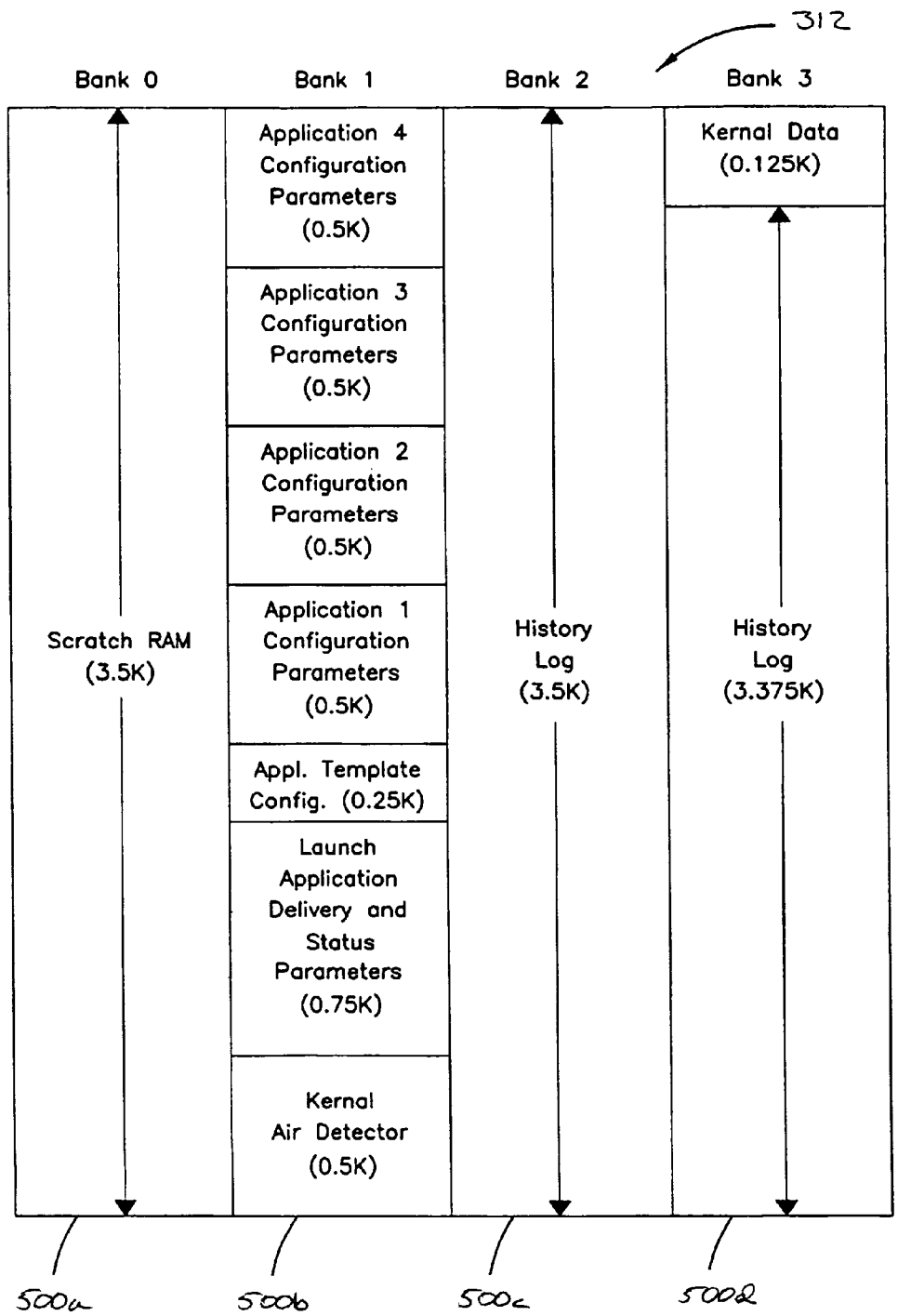

FIG. 5 illustrates the basic configuration of the RAM 312, which has four memory banks, Banks 0-3 500*a*-500*d*. Bank 0 500*a* is dedicated to a scratch memory. Bank 1 500*b* has four sets of addresses dedicated to configuration parameters for one of the application programs, a set of addresses dedicated to configuration of the application template, a set of addresses dedicated to the delivery status and parameters of the launch application, and a set of addresses dedicated to kernel data. Bank 2 500*c* is dedicated to a history log. Bank 3 500*d* is primarily dedicated to the history log. However, a set of addresses in Bank 3 500*d* is dedicated to kernel data.

The scratch memory serves as a second layer of buffer that provides protection if there is an error in the data being downloaded or if there is a power failure while data is being written to the RAM 312. During the write process, destination addresses will be designated to receive the data. However, data is first saved in the scratch memory. After the data is saved in the scratch memory, the application program analyses it to determine whether it has an errors or is otherwise corrupt. If the data is acceptable and doe not contain any errors that are detected by the application program, it will be saved to the destination addresses. In one embodiment, data is written to and read from the scratch memory in blocks using an error-checking scheme or algorithm such as cyclic redundancy code ("CRC").

A first flag will be set while data is being written to the scratch memory. A second flag is set after the write process is complete at which time it is written from the scratch memory to the destination addresses. Because the RAM 312 is a static RAM, either the first or second flag will be saved of the pump 110 has a power failure.

When power is returned to the pump 110, the flag will be read. If the first flag is set, the pump 110 either can disregard the data in the scratch memory or can complete the process of saving data to the scratch memory. If the second flag is set when power is returned to the pump 110, the pump 110 either can rewrite all of the data from the scratch memory to the destination address or can merely complete the write process from the scratch memory to the destination addresses.

An advantage of using the scratch memory in this manner is that the integrity of the data is maintained while being written to the RAM, which will help minimize the risk of a pump failure, faulty information being stored in the history log, or faulty program data being downloaded from the information management system 106 to the pump 110.

The scratch memory is also used for system diagnostics during power up. The boot program will initially test the scratch memory, which is Bank 0 500*a*. Data from Bank 1 500*b* is then transferred to the scratch memory so that the pump 110 can run diagnostics on that bank. A similar procedure is followed with banks 2 and 3 500*c* and 500*d*.

The four sets of addresses in Bank 1 500*b* for application configuration parameters are used to store persistent data, i.e., parameters that typically remain constant when a particular application program is being used. An example of such data might include the maximum and minimum flow rates or the maximum or minimum concentration settings.

A set of addresses for the application template configuration includes the data that is common between application programs. An application might include the lock level setting or a flag that activates the automatic lock level feature. Addresses for the delivery status and parameter of the launch program are used to store data that is not persistent, including various settings for the launch program. Examples of such data include the delivery rate and dosage. The history log is used to track various historical events such as a change in the delivery rate or when a pump 110 is powered up with time and date stamps.

Figure 6:
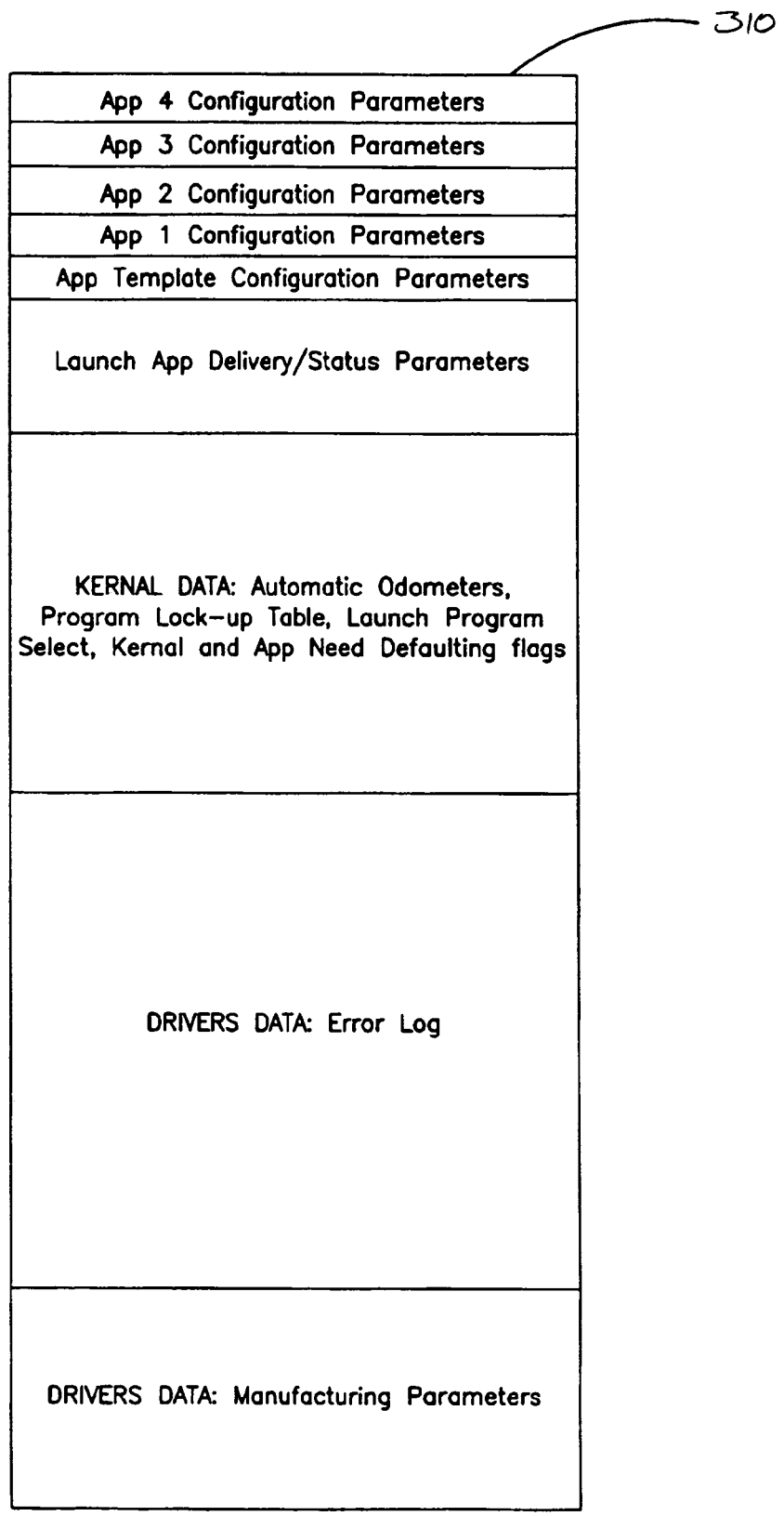

FIG. 6 illustrates the configuration of the EEPROM 310, which is less volatile than the RAM 312. Thus, the EEPROM 310 is used to store data that is more sensitive than the data stored in the RAM 312. Examples of such data include various look-up tables, manufacturer parameters such as the pump serial number, odometers that record data such as hours of use and amount of drug delivered, and an error log to record system faults and nonrecoverable errors. The EEPROM 310 has sets of addresses dedicated to application configuration parameters, application template configuration parameters, launch application delivery and status parameters, kernel data, error log, and manufacturing parameters.

Although the description set forth herein is directed to an exemplary embodiment of a pump 110, one skilled in the art will realize that the present invention can be embodied using many different types of programmable medical pumps. In fact, one possible embodiment includes an interface for communication between the pump 110 and the computer 104. The interface permits a single computer and its information management system 106 to interface with a variety of different programmable pumps, even pumps having different data structures and architectures.

The interface program will determine the type of pump 110 that is connected to the computer 104 and then facilitate data communication between the pump 110 and the database management system that handles requests for database actions. The interface program can convert data between the format required by the pump and the format required by the database.

Figure 8:
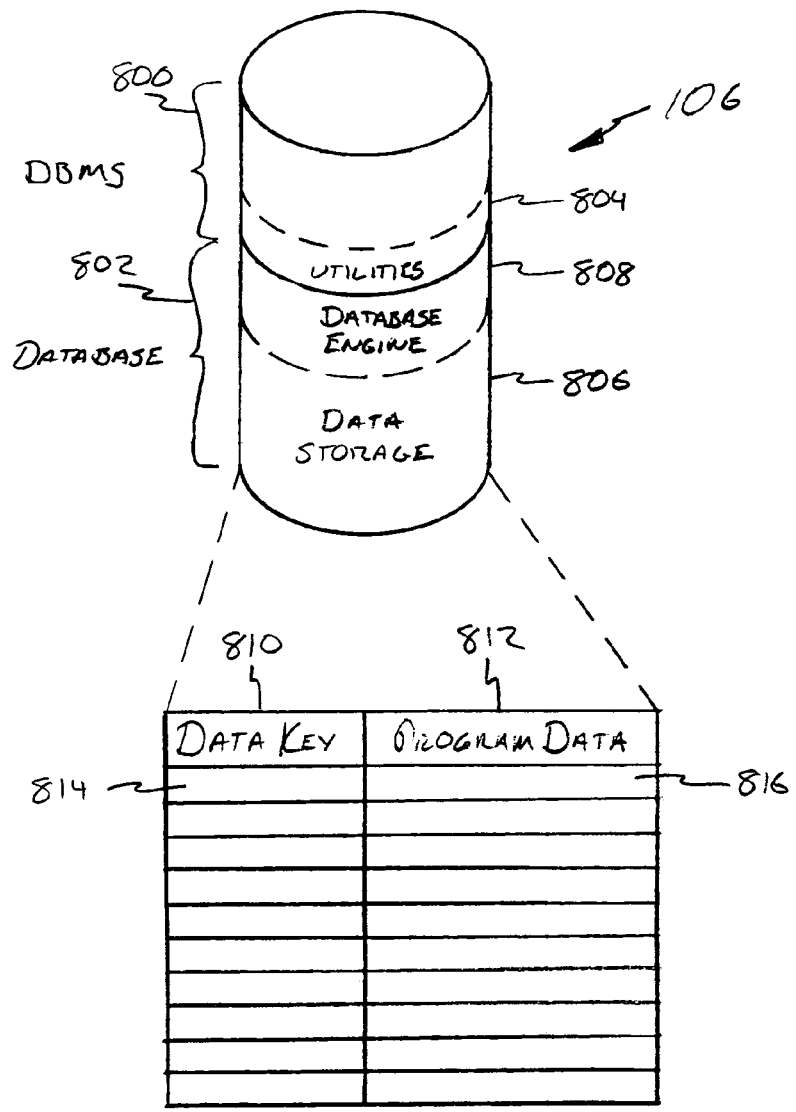
FIG. 8 illustrates the information management system shown in FIG. 1.

Referring to FIG. 8, the information management system 106 includes a database management system (DBMS) 800 and a database 802.

The DBMS 800 provides an interface between the database 802 and users of the database 802, including both the caregiver and the pump 110 itself. The DBMS 800 includes utilities 804 such as test utilities for performing diagnostics and system tests; communication protocols for providing communication between the information management system 106 and the pump's application programs; a diplomat, which will be described in more detail below, that tests the compatibility between the pump's programs and the information management system 106 before exchanging data. The database 802 includes a data storage area 806 and a database engine 808 for linking the DBMS 800 with data in the data storage area 806.

The information management system 106 can be programmed using any data manipulation language, including a structured query language (SQL). Additionally, any number of commercially available database application programs can be used to develop the pump management system. An example of a commercially available application program includes dBASE™, which is commercially available from dBASE, Inc. of Vestal, N.Y. Another database that can be used is Microsoft Access™, which is commercially available from Microsoft Corporation of Redmond, Wash.

Many possible embodiments and data structures for data in the data storage area 806 are possible. For example, the data can be structured using arrays, records, or linked lists. In one possible embodiment, the database 802 is a relational database that is formed with two data tables 810 and 812.

The first data table 810 contains a plurality of records 814 relating to data keys. Each data key identifies a set of program data that can be down loaded into a medical pump and includes three fields. The first field identifies the type of data key. In one possible embodiment they types of keys that are available include the name of a therapy, the name of a drug, and the name of a patient. The second field is the actual name of the data key that is meaningful to a caregiver (e.g., a patient's name). The third field is a unique identification formed from a string of characters.

The second data table 812 similarly includes a plurality of data records 816. Each record 816 is linked to at least one of the data keys of the first data table 810 and includes program data that sets parameters for the pump's 110 application program to run. The program data includes application configuration parameters and can include both persistent and non-persistent data. In one possible embodiment, each record includes data fields for persistent data such as a serial number; time and date parameters; programming unit parameters; concentration parameters; custom concentrations parameters, which is a list of concentration values for mg and mcg and their enabled state; continuous rate parameter; delivery limit parameter; delivery time parameter; demand dose amount parameter; dose counters clear flag, which clears the counters that track the number of times a bolus is request; demand dose lockout parameter, which sets the time minimum interval between bolus; given clear flag, which clears various odometers; reservoir volume parameter; air detector required parameter; air detector activated parameter; autolock parameter, which is a parameter establishing a lockout feature for the pump keyboard; beep enable parameter; clinician bolus code parameter, which is a code or password that allows a caregiver to administer a bolus according to parameters set up for the caregiver as opposed to the patient; date format parameter; epidural mode parameter; lock code parameter; lock level parameter; main display and power source status display parameters, which allow the caregiver to customize the information displayed on the pump display; custom data feature settings, including a list of features of the reported loop and their enabled status; maximum rate parameter, which is the maximum rate that the pump mechanism will deliver fluid; new patient marker parameter, which sets up the pump for new patient (e.g., clears patient event logs); pm interval parameter, which is a preventative maintenance interval; reservoir volume alert parameter; titration limit parameter; upstream sensor enable parameter; and custom text strings, which are character strings displayed on the pump display.

One skilled in the art will recognize that other possible embodiments of the Information Management System 106 and the database 802 are possible. For example, the program data can include any data that is related to the pump's 110 application programs or that is generally used in operation of the pump 110.

In yet another possible embodiment, the database includes program code for operation of the pump. In this embodiment, the database 802 could include an entire application program, or components of an application program such as an application template, application-specific code, a pump kernel, communication protocol, or various pump drivers. In this embodiment, the information management system 106 could automatically download and launch the pump's 110 application program rather than having a caregiver manually load and launch the application program. The information management system 106 could also automatically scan the memory system 304 in the pump 110 to ensure that the pump 110 is programmed with all of the relative software upgrades and download any upgrades that are not yet loaded onto the pump 110. The database can include other software or code that is not directly associated with the pump's 110 application program.

In yet another embodiment, the program data includes a flag or other information identifying an application program that the pump 110 should execute. When the program data is downloaded, the pump 110 detects this flag and automatically launches the predetermined application program from the flash memory 308.

Figure 7A:
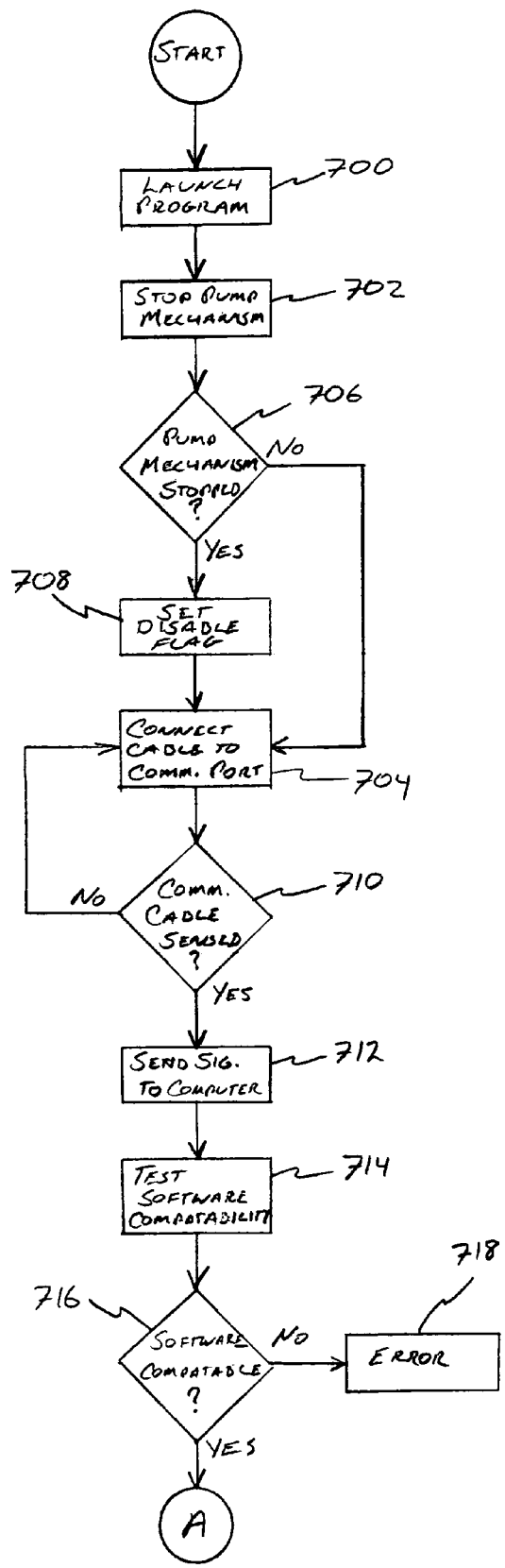
FIGS. 7A-7C is a flow chart illustrating operations executed by the computer and pump shown in FIGS. 2 and 3.
Figure 7B:
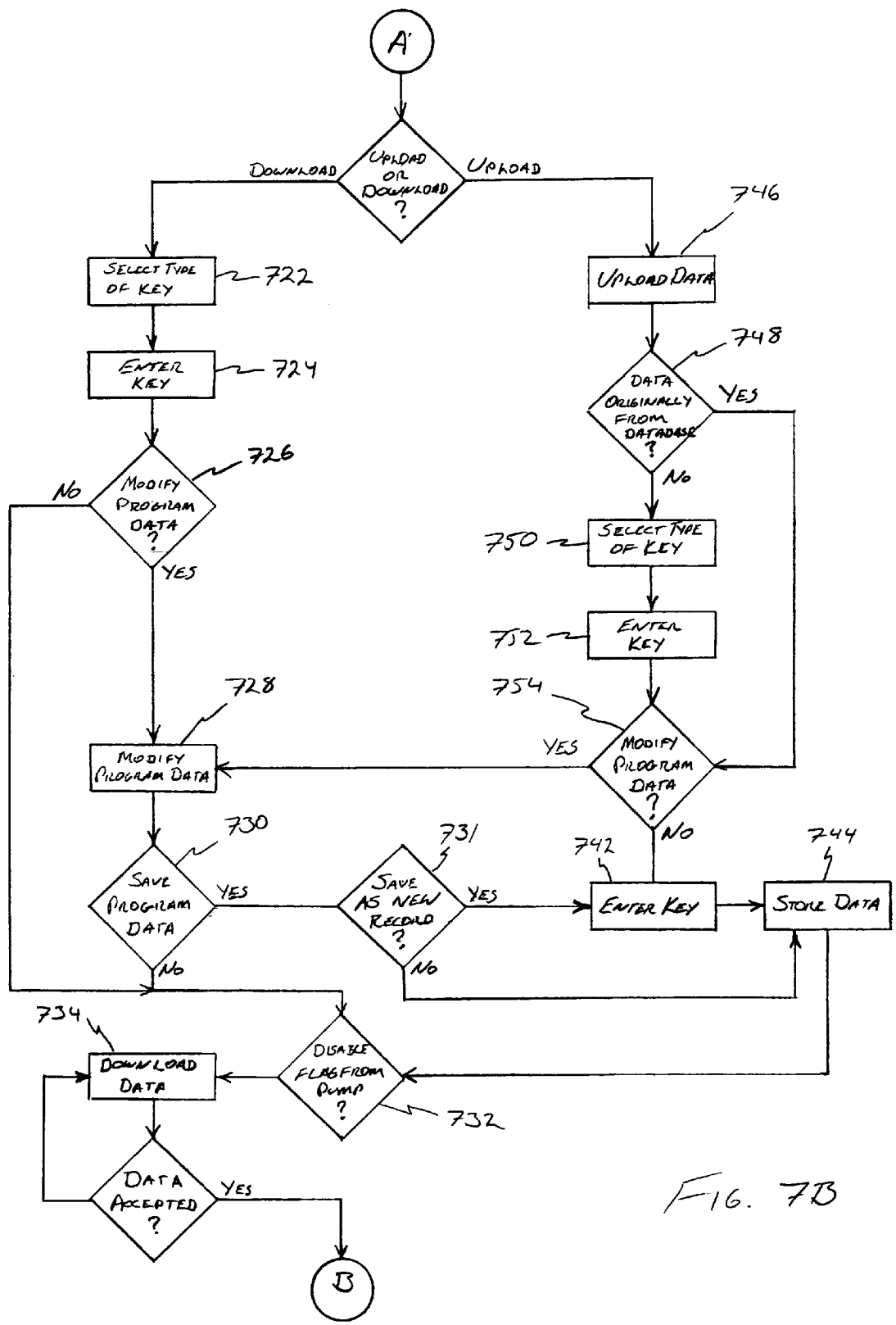
Figure 7C:
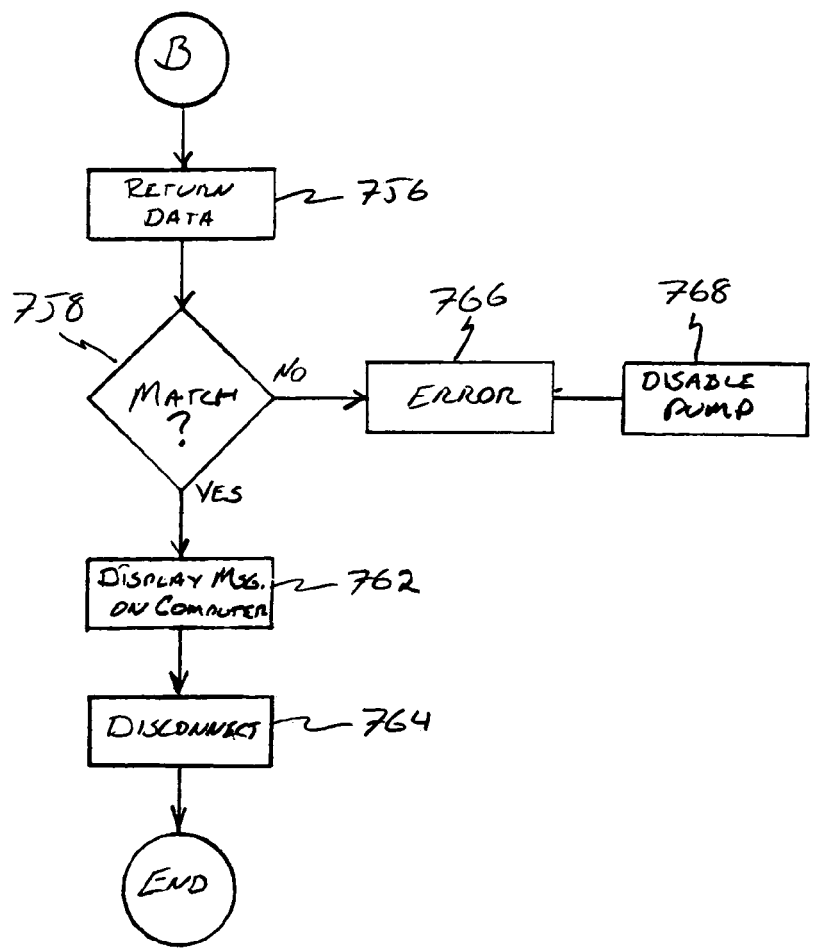

FIGS. 7a-7c illustrate one possible set of procedural steps followed when using a medical pump 110 and information management system 106 as described herein. Initially a caregiver launches the desired application program, operation 700, that is loaded in the flash memory 308 of the medical pump 110. Execution of the application program is then stopped operation 702, and the caregiver connects the communication cable from the computer 104 to the serial communication port 314 of the medical pump 110, operation 704. At operations 706 and 708, the pump kernel sets a disable flag if execution of the application program is stopped.

If the external communication sensor 334 detects the communication cable at operation 710, the pump kernel sends a signal to the information management system 106 that is loaded on the computer 104, operation 712. This action hails the computer. The pump 110 also enters into connect mode, and ion one possible embodiment, the application program is taken out of run mode so that they pump mechanism 306 is disabled. In one possible embodiment, the diplomat utility of the DBMS 800 receives the disabled flag and enters communication with the pump's 110 application program. In an alternative embodiment, the diplomat utility enters into communication with a test utility loaded on the medical pump 110. This alternative embodiment might be used if the batch download process described herein will download program code to the pump 110 as well as program data. At operations 714 and 716, the diplomat utility in the DBMS 800 receives information about the version of application program loaded on the pump 110 and determines whether the information management system 106 is compatible with the pump's 110 application software. Similarly, the test utility on the pump 110 receives information about the information management system 106, and determines whether it can interface with the information management system 106. If either of the diplomat utility of DBMS 800 or the pump's 110 test utility determines that there is no compatibility, the utility detecting the incompatibility will generate an error, operation 716, and no program data will be communicated between the database 802 of the information management system 106 and the pump 110.

Referring to FIG. 7B, if the information management system 106 and the pump's 110 application program are compatible, the DBMS 800 generates a user interface, prompting the caregiver to choose between downloading program data to a pump 110 or uploading program data from a pump 110 into the database 802, operation 720. There are a variety of scenarios in which a caregiver might choose whether to upload or download program data.

For example, the caregiver might choose to download data to the pump 110 to use preexisting data that is already stored in the database 802. This procedure saves the caregiver time because he or she will not have to individually program each data item. The caregiver might choose to upload data from a pump 110 to clone a pump's programming for future use with that same pump or with other pumps. The caregiver might also choose to upload data if it is necessary to modify some of the program data. Uploading the data allows the caregiver to edit the data using the keyboard 234 and mouse 236 on the computer 104, which can be more efficient than indexing through each of the program data items using the keyboard on the pump 110. Although one can create a record in the database 802 by cloning an existing pump, the caregiver can also create a record by entering data into the database 802 using the keyboard 234 and mouse 236 on the computer 104.

If the caregiver chooses to download data from the database 802 of the information management system 106 to the pump 110, he or she will select the type of data key to be used in retrieval of the desired set of program data and then enter the data key, operations 722 and 724. In one possible embodiment, there are three types of data keys that the user can select and use—the patient, therapy, or drug. The caregiver can enter the data in several formats. For example, one possible embodiment allows the caregiver to enter the name of the data key in prose (e.g., "John Doe" for a patient, "morphine" for a drug). In another embodiment, the caregiver enters an I.D. for the data key. The I.D. is an alpha/numeric character string and can be entered using the computer keyboard 234. Alternatively, the computer 104 might include a scanner 112 and related utilities. The drug, patient, or therapy might have an I.D. embodied in a bar code that the caregiver scans. A utility or some other program module then communicates the scanned I.D. to the DBMS 800, which retrieves the set of program data associated with the data key. The program data is retrieved from the second table 812 of the database 802.

At operations 726 and 728, the caregiver can edit the program data received from the database 802. The caregiver might edit the data for a variety of reasons. For example, the caregiver might edit dose requirements based on the patient weight or amount of pain the patient is experiencing.

At operation 730, the caregiver determines whether to save the edited data. If the caregiver chooses to save the edited data, he or she must decide, operation 731, whether to overwrite the existing set of program data or save the data as a new set of program data. If the caregiver chooses to overwrite the existing program data, he or she will activate a save button on the user interface and operation 744 will store the edited program data by overwriting the set of program data that was originally retrieved from the database 802. If the caregiver chooses to save the edited program data as a new record and preserve the program data originally retrieved form the database 802, he or she will enter a new data key, operation 742, and then activate a button on the interface to instruct the DBMS 800 to save the new data key in the first data table 810 and to save the edited set of program data as a new record in the second data table 812 and to link the new record to the new data key.

At operation 732 the application program of the pump program manager determines whether the pump sent a disable flag to the computer. If the disable flag was received, operation 734 downloads the program data to the pump 110 using the scratch memory as described above. In one possible embodiment, the data key is also downloaded to the pump so that the program data can be easily identified.

In one possible embodiment, however, the type of edited program data that can be downloaded to the pump 110 is limited if the pump 110 is not disabled and the pump is still in the run mode (i.e., the pump mechanism 306 is still running). In such an embodiment, for example, the only modified program data that can be downloaded to the pump 110 is data defining the delivery rate for the fluid, bolus amount, time between boluses, and volume delivered limit. In such an embodiment, if the disable flag is not set, the application program compares the program data that is being edited to a list of permissible data changes, operation 736. If any of the requested data changes are not found in the list of permissible data changes, the application program rejects the data that was downloaded from the information management system 106 and sends a rejected-data signal to the DBMS 800. In one possible, embodiment the information management system automatically attempts to re-download the data to the pump 110. In an alternative embodiment, the information management system generates an error that is displayed on the monitor 242. If all of the data changes are found in the list of permissible data changes, and there are not other errors in the data that are detected by the application program, the pump will accept the data and transfer the data from the scratch memory to its destination addresses.

If the caregiver chooses to upload program data from the pump 110 to the information management system 106, the caregiver activates an upload data button on the user interface of the information management system 106 on the computer 104. At operation 746, the program data is uploaded from the pump 110 to the information management system 106. At operations 748 the DBMS 800 determines whether the program data was originally retrieved from the database 802. In one possible embodiment, if the program data was originally loaded on the pump 110 from the database 802 of the information management system 106, the data key that identifies the program data is also uploaded from the pump 110 to the information management system 106. If the program data was originally programmed on the pump 110 and not previously downloaded from the database 802 of the information management system 106, the DBMS 800 prompts the user to select a type of data key, operation 750, and to enter a data key, operation 752.

At operation 754, the caregiver then chooses whether to edit the program data that was uploaded form the pump 110. If the caregiver chooses to modify the program data, operation 728 is executed as described above. If the caregiver chooses to not modify the program data, operation 742 is executed as described above.

In one possible embodiment, when data including the program data is downloaded to the pump 110 at operation 734, the DBMS 800 maintains the program data in RAM 210 regardless of whether the program data is saved in the database 802 at operation 744. After the data is downloaded to the pump 110, operation 734, the pump 110 returns the program data to the DBMS 800, which compares the returned program data to the program data temporarily stored in RAM 210. At operations 758-764, if program data returned from the pump 110 and the program data temporarily stored in RAM 210 match, a utility executed by the computer 104 generates a message on the computer display 242 stating the pump 110 was successfully programmed operation 762. The caregiver then disconnects the pump 110 from the computer at operation 764. If the program data returned by the pump 110 does not match the program data temporarily stored in RAM 210, at operation 766 the DBMS 800 generates an error and communicates the error to the pump 110. If the pump 110 receives this error, the application program will not accept the data downloaded from the information management system.

As one skilled in the art will appreciate, there are many possible alternative embodiments to the systems, hardware platforms, and programs disclosed herein. The operations described above can be executed in different order, can include operations that are not described herein, and can exclude operations that are described herein.

Furthermore, the invention described herein can be used in a variety of different environments and in a variety of different applications. For example, the system can be used in a hospital, nursing home, clinic, or any other environment. The system also can be used across more than one facility. For example, a pharmacist might create a set of program data and then download it into the database 802. A caregiver can then access that set program data for programming and management of the pumps 110. Similarly, access to the database 802 can be through a standalone computer, through a computer directly linked to a local network 108, or through a computer remotely linked through a wide area network such as the Internet 116.

In yet another embodiment, the program data can be loaded into a palm-held computing platform such as the Symbol PPT 2700 Series Pocket PC as described above. The palm-held computer has a local database that can be synchronized with the database 802 of the information management system 106. In this embodiment, the palm-held computer has a scanner and can scan a bar code on a drug package such as an I.V. bag or a patient I.D. one a wristband. The related program data is then retrieved from a database locally stored on the palm-held computer and is downloaded to the pump 110. Alternatively, the caregiver can upload data, including the program data and data key, from the pump 110 to the hand-held PC. The data can then be locally stored in the palm-held computer. The database local on the palm-held computer can be synchronized with the database 802 on the information management system 106.

The various embodiments described above are provided by way of illustration only and should not be construed to limit the invention. Those skilled in the art will readily recognize various modifications and changes that may be made to the present invention without following the example embodiments and applications illustrated and described herein, and without departing from the true spirit and scope of the present invention, which is set forth in the following claims.

The claimed invention is:

1. A patient care system comprising:
    a medical infusion pump adapted to pump fluid to a patient, the medical infusion pump including a memory comprising a previously loaded application program for controlling operation of the pump;
    a network communicatively coupled with the medical infusion pump and a database, the database comprising a plurality of program data records and a plurality of patient-specific data key records, wherein at least one patient-specific data key record is associated with at least one program data record in the database; and
    an input device communicatively coupled with the medical infusion pump and adapted to receive patient-specific data corresponding to at least one patient-specific data key record stored in the database,
    wherein the program data record associated with the corresponding patient-specific data key record is communicated from the database to the memory of the medical infusion pump, the program data record comprising one or more operating parameters configured to control the previously loaded application program.

2. The system of claim 1, wherein the patient-specific data key record contains a data key and each data key identifies at least one program data record.

3. The system of claim 1, wherein the data key is an I.D. embodied in a bar code associated with at least one of:
    the patient;
    a drug prescribed to the patient; and
    a therapy prescribed to the patient.

4. The system of claim 1, wherein the data key is an alphanumeric character string associated with at least one of:
    the patient;
    a drug prescribed to the patient; and
    a therapy prescribed to the patient.

5. The system of claim 1, wherein the program data record contains program data comprising parameters about the patient.

6. The system of claim 5, wherein the parameters about the patient are at least one of:
    the patient's age;
    the patient's weight;
    a prescribed delivery schedule;
    a prescribed dose requirement; and
    parameters limiting the size and frequency of a bolus that the patient can self administer.

7. The system of claim 1, wherein the program data record is created by a pharmacist.

8. The system of claim 1, wherein the input device is a scanner.

9. The system of claim 8, wherein the scanner is hand-held.

10. The system of claim 8, wherein the scanner is adapted to scan a barcode on at least one of:
    an I.V. bag;
    a medicine package; and
    a patient wristband.

* * * * *